United States Patent
Nestor, Jr.

(10) Patent No.: US 12,303,115 B2
(45) Date of Patent: May 20, 2025

(54) ENDOSCOPIC TISSUE INVERSION AND RESECTION SYSTEM AND METHOD OF RESECTING TISSUE

(71) Applicant: de la Cruz-Munoz Nestor, Jr., Miami, FL (US)

(72) Inventor: de la Cruz-Munoz Nestor, Jr., Miami, FL (US)

(73) Assignee: University Of Miami, Miami, FL (US)

( * ) Notice: Subject to any disclaimer, the term of this patent is extended or adjusted under 35 U.S.C. 154(b) by 0 days.

(21) Appl. No.: 18/751,115

(22) Filed: Jun. 21, 2024

(65) Prior Publication Data
US 2024/0398395 A1 Dec. 5, 2024

Related U.S. Application Data

(63) Continuation of application No. PCT/US2023/028626, filed on Jul. 25, 2023.
(Continued)

(51) Int. Cl.
*A61B 1/04* (2006.01)
*A61B 17/00* (2006.01)
(Continued)

(52) U.S. Cl.
CPC .......... *A61B 17/00234* (2013.01); *A61B 1/04* (2013.01); *A61B 34/73* (2016.02);
(Continued)

(58) Field of Classification Search
CPC ..... A61B 1/04; A61B 17/00234; A61B 34/73; A61B 2034/731; A61B 2017/00296;
(Continued)

(56) References Cited

U.S. PATENT DOCUMENTS 6,352,503 B1   3/2002  Matsui et al.
7,338,503 B2   3/2008  rosenberg et al.
(Continued)

FOREIGN PATENT DOCUMENTS

WO   2021234508 A1   11/2021

OTHER PUBLICATIONS

USPTO, International Search Report and Written Opinion of the International Searching Authority, Feb. 20, 2024, for PCT/US2023/028626.

*Primary Examiner* — Timothy J Neal
*Assistant Examiner* — William B Chou
(74) *Attorney, Agent, or Firm* — Invention To Patent Services; Alex Hobson (57) ABSTRACT

An endoscopic tissue inversion and resection system employs an exemplary endoscopic tissue inversion and resection device configured to invert tissue to plicate the tissue between a pair of clamping tubes that advance a clamp component and guide clamp components around the plicated tissue. A clamp component may include magnets and/or a shape memory material. The magnets may produce a pinching force of the tissue. A shape-memory clamp component may have a preform shape that when configured around the plicated tissue clamps and retains the plicated tissue. An endoscope is configured between the first clamping tube and a second clamping tube and a tissue grasping device plicates the tissue. The endoscope may have an imaging device, to enable viewing of the interior of the body during a procedure to guide the endoscope to a desired location.

18 Claims, 11 Drawing Sheets

Related U.S. Application Data

(60) Provisional application No. 63/470,868, filed on Jun. 3, 2023.

(51) Int. Cl.
*A61B 34/00* (2016.01)
*A61B 17/22* (2006.01)

(52) U.S. Cl.
CPC .............. *A61B 2017/00296* (2013.01); *A61B 2017/00349* (2013.01); *A61B 2017/00358* (2013.01); *A61B 2017/00867* (2013.01); *A61B 2017/00876* (2013.01); *A61B 2017/22038* (2013.01); *A61B 2034/731* (2016.02)

(58) Field of Classification Search
CPC ........... A61B 2017/00349; A61B 2017/00358; A61B 2017/00867; A61B 2017/00876; A61B 2017/22038
See application file for complete search history.

(56) References Cited

U.S. PATENT DOCUMENTS

| | | | |
|---|---|---|---|
| 2006/0241691 A1 | 10/2006 | Wilk | |
| 2010/0113873 A1 | 5/2010 | Takayuki et al. | |
| 2014/0163664 A1* | 6/2014 | Goldsmith | A61B 17/0057 604/93.01 |
| 2022/0015787 A1 | 1/2022 | Schembre et al. | |
| 2024/0277371 A1* | 8/2024 | Gagner | A61B 17/12013 |

* cited by examiner

ENDOSCOPIC TISSUE INVERSION AND RESECTION SYSTEM AND METHOD OF RESECTING TISSUE

CROSS REFERENCE TO RELATED APPLICATIONS

This application is a continuation of international application No. PCT/2023/028626 having an international filing date of Jul. 25, 2023, which claims the benefit of priority to 63/470,868, filed on Jun. 3, 2023; the entirety of which is hereby incorporated by reference herein.

BACKGROUND OF THE INVENTION

Field of the Invention

The invention relates to an endoscopic tissue inversion and resection system that employs an exemplary endoscopic tissue inversion and resection device configured to invert tissue to form plicate tissue between a pair of clamping tubes that advance clamp components out of said clamping tubes and along opposing sides of the plicated tissue to clamp and retain the tissue in a plicated configuration.

SUMMARY OF THE INVENTION

The invention is directed to an endoscopic tissue inversion and resection system that employs an exemplary endoscopic tissue inversion and resection device configured to invert tissue to form plicated tissue between a pair of clamping tubes that advance clamp components, such as shape-memory clamp components and/or magnets out of opposing first clamping tube and second clamping tube to clamp and retain the tissue in a plicated configuration. A tissue grasping device may be advanced from the endoscope and couple with the tissue to pull the tissue toward the endoscope to plicate the tissue. A plurality of magnets may be advanced out of the distal ends of the first clamping tube and second clamping tube and may be coupled with a guide extension to ensure proper placement and alignment across the plicated tissue. A shape-memory material may be advanced out of the distal end of the first clamping tube and into the distal end of the second clamping tube, guided by a guide extension and the shape-memory clamp component may have a bend portion that forms a bend at the distal end of the plicated tissue to clamp the plicated tissue. A pair of clamp components may be configured in the opposing pair of clamping tubes and coupled together by couplers, distal and/or proximal couplers, to form a clamping arrangement of the pair of clamp components around the plicated tissue. A clamp component may be a magnetic clamp component, a shape memory clamp component, a clamp component that includes a plurality of portions that are joined together by a coupler or some combination thereof.

An exemplary endoscopic tissue inversion and resection device has an endoscope configured between the first clamping tube and the second clamping tube. The first clamping tube and second clamping tube may extend out distal from the distal end of the endoscope to provide a clamping restraint or guide as the tissue is inverted by pulling the tissue up through the first clamping tube and second clamping tube to form plicated tissue between the first and second clamping tubes. The endoscope may have an imaging device, such as a camera to enable viewing of the interior of the body during a procedure to guide the endoscope to a desired location. The distal end of the endoscope may have a distal end opening from which a tissue grasping device is advanced to plicate tissue by pulling the tissue toward the endoscope and between the first clamping tube and second clamping tube. A guide extension, such as a suture or guide wire, extends down along the first clamping tube, out the distal end of the first clamping tube, over to the distal end opening of the second clamping tube and back along the second clamping tube. The guide extension has a loop portion between the distal ends of the first and second clamping tubes.

The endoscopic tissue inversion and resection device has a first clamping tube and second clamping tube that may be configured to move down or away from the endoscope to configure the tubes on opposing sides of tissue to guide the tissue through the first and second clamping tubes to plicate the tissue. A tissue grasping device, such as a hook, or corkscrew, pulls the tissue up between the first clamping tube and second clamping tube and may extend from the end of the endoscope. The first clamping tube and second clamping tube may be moved away from the endoscope by an actuator and a pivot point may allow the first and second clamping tubes to rotate away from the endoscope. The first clamping tube and second clamping tube may be made of a shape-memory material, or alloy, such as Nitinol and may be restrained along the endoscope until the endoscope is positioned in a desired location, at which time the first and second clamping tubes can be unrestrained and move automatically away from the endoscope. A sheath may extend over the endoscope or the first and second clamping tubes and may restrain the first clamping tube and second clamping tube to the endoscope and pulling the sheath back toward the proximal end of the endoscope may release the first and second clamping tubes. The first and second clamping tubes may also be restrained by individual restraints and sliding these restraints back or advancing the tubes through the restraints may move the first and second clamping tubes into position away from the endoscope. The first clamping tube and second clamping tubes may further be actuated toward each other after the tissue is plicated to pinch and clamp the plicated tissue to restrain the plicated tissue.

An endoscopic tissue inversion and resection device may be a magnetic endoscopic tissue inversion and resection device employing magnets as the clamp components. Magnets may be coupled with a guide extension, such as a suture or guide wire, that extends down the first clamping tube, out from the distal end of the first clamping tube and into the distal end of the second clamping tube. A magnet may have an aperture and the guide extension may extend through this aperture to couple the magnet to the guide extension. A magnet may be advanced along the first clamping tube and second clamping tube by a respective advancer, such as a rod or wire extending into the respective clamping tube, and then be expelled from the distal end of the respective clamping tube. The magnets may be coupled with the guide extension to enable some additional means to position the magnets by manipulation of the guide extension.

A plurality of magnets may be configured within the clamping tubes prior to insertion of the endoscope, or a single magnet may be advanced along the clamping tubes before a second magnet is inserted therein. Plicated tissue may be restrained or clamped together by a suitable number of magnets on each side of the plicated tissue, such as at least one, two or more, three or more, five or more, ten or more and any range between and including the number provided.

The magnets may be permanent magnets and may be coated with a material such as a polymer to prevent reaction with the tissue. A fluoropolymer coating may be used to reduce friction such that the magnets slide easily through the clamping tubes and to also aid in biocompatibility. The permanent magnets may be Neodymium magnets which are strong permanent magnets made from an alloy of neodymium, iron and boron. Pull Force is the amount of force required to separate two of the same size magnets from each other. An exemplary magnet may have a magnetic strength that is suitable to clamp the tissue but not so strong that the tissue undergoes necrosis before the resected tissue is healed together. Magnetic strength may be measured by pull force, the force required to separate or pull apart two of the same magnets. Exemplary magnets may have a pull force of about 133 N (30 lbs) or more, about 133 N (30 lbs) or less, about 89 N (20 lbs) or more, about 89 N (20 lbs) or less, about 44.5 N (10 lbs) or more, about 44.5 N (10 lb) or less, about 22.24 N (5 lbs) or more, about 22.24 N (5 lbs) or less and any range between and including the pull force values provided.

The magnets may have interconnect features such hooks or interference fit features that couple a first magnet to a second magnet on a first and or second side of the plicated tissue. The magnets may be coupled together when in the clamping tube or may be separated and then coupled together when a second magnet is expelled from the distal end of the clamping tube. Also, the magnets may be self-orienting having surfaces to ensure that the magnets orient along the plicated tissue in a proper orientation and may comprise flat surfaces, or curved surfaces, wherein a first magnet on a first side of the plicated tissue has a convex surface along the plicated tissue and an opposing first magnet on a second side of the plicated tissue has a concave surface to receive and nest with the convex surface of the first side first magnet to clamp the resected tissue therebetween. The magnets may have a non-uniform cross-sectional geometry or dimension along the length of the magnet, length extending linearly along the plicated tissue from a distal end to a proximal end. Also, the magnets may have a high friction type surface or surface features to prevent the magnets from slipping, such as barbs or other features that taper or taper to a point that is configured to penetrate into the plicated tissue. A first barb may extend in a first direction and a second barb may extend in an opposing direction to said first barb, to prevent movement of the magnet along the plicated tissue.

The endoscopic tissue inversion and resection device may have an interface controller that allows a surgeon to manipulate the endoscope and clamping tubes as well as advancers and clamp components, such as magnets, or shape memory clamp components for the procedure. The interface controller may have a tube actuator controller, that may be used to actuate the first clamping tube and second clamping tube away from the endoscope for plicating the tissue. As described herein, this tube actuator controller may be coupled with a sheath that is pulled back to allow the shape memory tubes to move into a required position automatically upon removal of the restrain from the sheath. A tissue grasper controller may be used to either advance the tissue grasping device and/or actuate a grasper, such as a clamp. The interface controller may have ports or openings to insert clamp components, such as magnets, into the first clamping tube and/or second clamping tube.

After the opposing magnets are configured on opposing sides of the plicated tissue, the guide extension can be removed. The plicated tissue may be resected leaving plicated tissue clamped together by the magnets. This clamped tissue may undergo necrosis and the tissue may heal together.

The magnetic endoscopic tissue inversion and resection system may be used for resecting portions of the stomach for weight loss, removal of tumors, ulcers, and the like.

An exemplary endoscopic tissue inversion and resection device includes an endoscope configured between a first clamping tube and second clamping tube. A first clamp component may extend in the first clamping tube and a second clamp component may extend in the second clamping tube, both coupled to the guide extension that extends through each of the clamping tubes and forms a loop portion between the distal end opening of the first clamping tube and the distal end opening of the second clamping tube. Each of the first clamp component and second clamp components may be advanced out of the respective distal end openings of the clamping tubes by an advancer, guided by the guide extension, and may couple together on the distal end of the plicated tissue by a distal coupler, which may be an integral coupler comprising a coupler on one or more of the first and second clamp components. The clamping tubes may be retracted to align the first clamp component and second clamp component on opposing sides of the plicated tissue.

The proximal ends of the first and second clamp components may be coupled together on the proximal end of the plicated tissue by a proximal coupler and again, this may be an integral coupler including couplers on one or both of the first and second clamp components.

The first and second clamp components may be tubes that extend over the guide extension, suture or guide wire for example, and the distal coupler may be formed when the first clamp component is advanced into or over the second clamp tube. Barbs or hooks on the first clamp component may hook into respective apertures or coupler receivers in the second clamp component. In this way, the two distal ends of the first and second clamp components may be coupled by simply advancing the distal end into each other. One of the clamp components may be tapered and the other clamp component may have a flared distal end to aid in the advancement of one into the other for coupling. Note the first and/or second clamp component may not be a tube but may be coupled to the guide extension for directing the clamp component around the distal end of the plicated tissue. The first and/or second clamp component may be shape-memory material that causes the clamp components to retain a clamping configuration around the plicated tissue.

An endoscopic tissue inversion and resection device may utilize a single clamp component that is a shape-memory material having a bend portion forming a bend around the distal end of the plicated tissue to extend the shape-memory clamp component along opposing sides of the plicated tissue, to clamp the plicated tissue. The shape-memory clamp component may be retained and guided by the first clamping tube and by the guide extension extend from the distal end of the first clamping tube to the distal end of the second clamping tube. The shape-memory clamp component may automatically hold a bent shape along the bend portion as the clamping tubes are retracted. The bend portion may be a bend in the shape-memory clamp component that is at least 180 degrees bend. The bend portion may form a bend that is more than 180 degrees to produce a clamping force on the plicated tissue when configured around the plicated tissue. Again, the shape-memory clamp component may be a tube or have a tube portion that extends over the guide extension.

The shape-memory clamp components or components may be a shape-memory alloy, such as nitinol, that can be deformed from a preformed shape and then return to the preformed shape upon removal of a deforming force. The shape-memory clamping tube may be deformed to enable it to be advanced through the clamping tube or tubes and then assume the preform shape when released from the clamping tube or tubes. In an exemplary embodiment, a single shape-memory clamp component forms a horse-shoe shaped around the plicated tissue. A shape-memory alloy (SMA) is an alloy that can be deformed when cold but returns to its pre-deformed ("remembered") shape when heated, such as to body temperature.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 1:
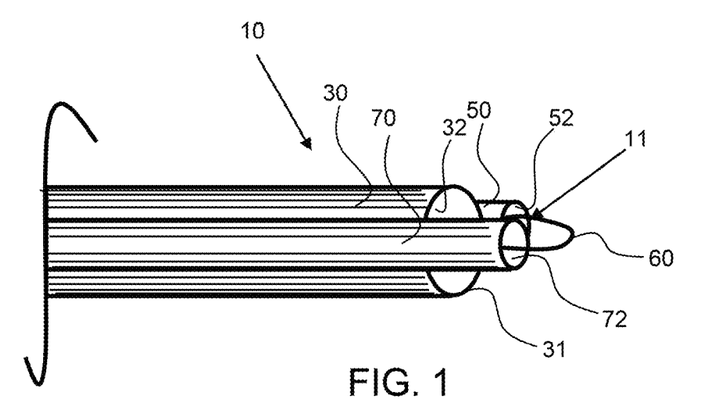
FIG. 1 shows a side perspective view of an exemplary magnetic endoscopic tissue inversion and resection device having an endoscope configured between a first clamping tube and second clamping tube.
Figure 2:
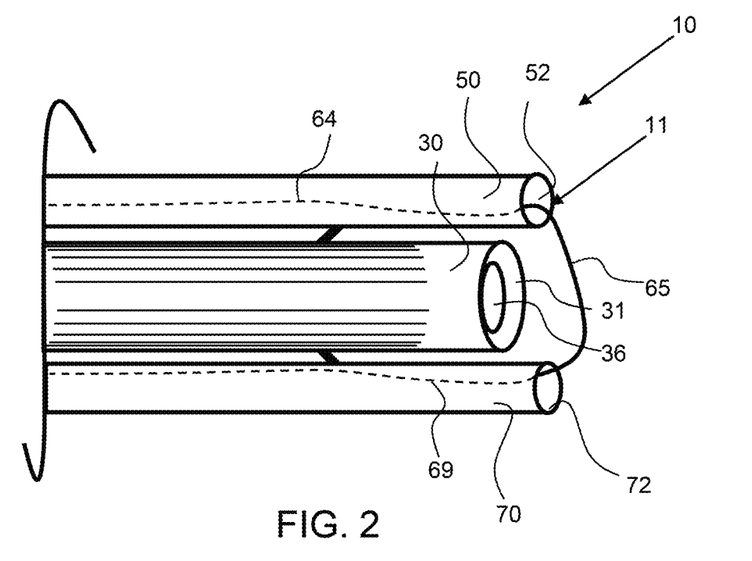
FIG. 2 shows a top perspective view of an exemplary magnetic endoscopic tissue inversion and resection system having an endoscope configured between a first clamping tube and second clamping tube.

Referring to FIGS. 1 and 2, an exemplary magnetic endoscopic tissue inversion and resection device 11 has an endoscope 30 configured between a first clamping tube 50 and second clamping tube 30. The first clamping tube and second clamping tubes may extend out distal from the distal end 31 of the endoscope. The endoscope may have an imaging device 36, such as a camera for enabling viewing of the interior of the body during a procedure. The distal end 31 of the endoscope may have a distal end opening 32 on the distal end 31 from which a tissue grasping device is advanced to plicate tissue by pulling the tissue toward the endoscope and between the first clamping tube 50 and second clamping tube. A guide extension 60 extends down along the first clamping tube 50, out the distal end opening 52 of the first clamping tube, over to the distal end opening 72 of the second clamping tube 70 and back along the second clamping tube. The guide extension 60 has a loop portion 65 between the distal ends of the first and second clamping tubes.

With reference not to FIGS. 3 to 10, an exemplary magnetic endoscopic tissue inversion and resection system 10 utilizes a magnetic endoscopic tissue inversion and resection device 11 to restrain plicated tissue 22 with magnets configured on either side of the plicated tissue. The magnetic endoscopic tissue inversion and resection device 11 has the first clamping tube 50 and second clamping tube 70 moved down from the endoscope 30 and configured on opposing sides of plicated tissue 22, wherein the tissue 20 is plicated by a tissue grasping device 40, such as a hook 43, that engages the tissue at a tissue grasping location 27, between the first clamping tube 50 and second clamping tube 70, and pulling the tissue 20 up between the first clamping tube and second clamping tube. Note that the guide extension 60 is extending out from the distal end opening 52 of the first clamping tube 50 and distal end opening 72 of the second clamping tube 70. An actuator 77, such as a pivot or guide may be used to actuate the first and second clamping tube away from the endoscope and proximal to the tissue 20 to enable plicating the tissue. Also, the first clamping tube 50 and second clamping tube 70 may be made out of a shape memory material or alloy, such as Nitinol and sliding back a sheath 38 over the first clamping tube 50 and second clamping tube 70 may allow the tubes to automatically move into position away from the endoscope 30.

Figure 3:
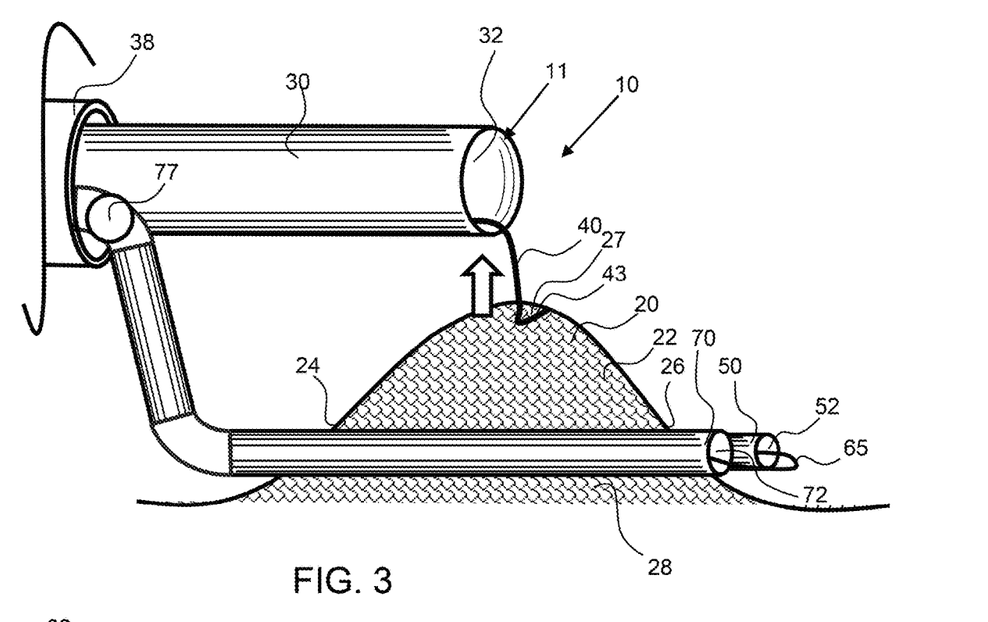
FIG. 3 shows a side perspective view of an exemplary magnetic endoscopic tissue inversion and resection device having the first clamping tube and second clamping tube moved down from the endoscope and configured on opposing sides of plicated tissue, wherein the tissue is plicated by a tissue grasping device pulling the tissue up between the first clamping tube and second clamping tube.

As shown in FIG. 3, the plicated tissue 22 has a distal end 26 and proximal end 24, and the second side of the plicated tissue is shown. The first clamping tube 50 and second clamping tube 70 are configured with the distal end openings extending past the distal end of the plicated tissue and the guide extension 60 extends around the distal end of the plicated tissue from the first clamping tube 50 and second clamping tube 70. The first clamping tube 50 and second clamping tube 70 are configured along the base 28 of the plicated tissue 22.

Figure 4:
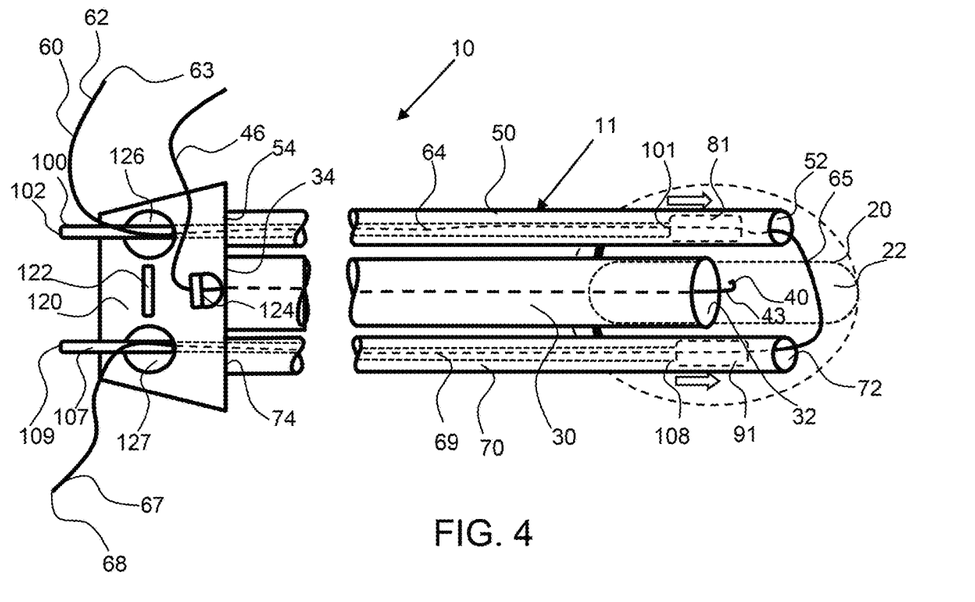
FIG. 4 shows a top perspective view of an exemplary magnetic endoscopic tissue inversion and resection system with a first side magnet and second side magnet being advanced through the first clamping tube and second clamping tube, respectively, by advancers, wherein the magnets are retained to a guide extension that extends along both the first clamping tube and second clamping tube and loops between them from the distal end of the first clamping tube and second clamping tube.

As shown in FIG. 4, a first magnet 81 is configured in the first clamping tube 50 and is being advanced along the first clamping tube by a first side advancer 100 that is pushed or advanced into the first clamping tube wherein the distal end 101 of the first side advancer pushes the first magnet 81 along the first clamping tube 50. The first side advancer extends out from a first side tube opening 126 in the interface controller 120 on the proximal end 54 of the first clamping tube. Likewise, a first magnet 91 is configured in the second clamping tube 70 and is being advanced along the second clamping tube by a second side advancer 107 that is pushed or advanced into the second clamping tube, wherein the distal end 108 of the second side advancer 107 pushes the first magnet 91 along the second clamping tube 70. The second side advancer extends out from a second side tube opening 127 in the interface controller 120 on the proximal end 74 of the second clamping tube. The proximal end 102, 109 of the first and second advancers, respectively, extend out from the interface controller 120. A sheath may be withdrawn to enable the first and second clamping tubes to actuate away from the endoscope.

Also shown in FIG. 4 is the guide extension 60 that extend from a first side exposed portion 62 having a first side proximal end 63, along the first clamping tube 50 as a first tube extension portion 64, out of the distal end opening 52 of the first clamping tube, along a loop portion 65 between the distal end opening 52 of the first clamping tube and distal end opening 72 of the second clamping tube 70, along the second clamping tube 70 as the second tube extension 69, and out of the interface controller 120 to an second side exposed portion 67 having a second side proximal end 68. The first side first magnet 81 and second side first magnet 91 may be coupled to the guide extension for guidance and placement along the plicated tissue. The magnets may have an aperture and the guide extension 60 may extend through the aperture in the magnets.

The proximal end 34 of the endoscope 30, as well as the proximal end 54 of the first clamping tube 50 and proximal end 74 of the second clamping tube 70 may couple with an interface controller 120 that may have a clamping tube actuator controller 122, that may be used to actuate the first clamping tube and second clamping tube away from the endoscope 30 for plicating the tissue 20. A tissue grasper controller 124 may be used to either advance the tissue grasping device 40 and/or actuate a grasper, such as a clamp.

Figure 5:
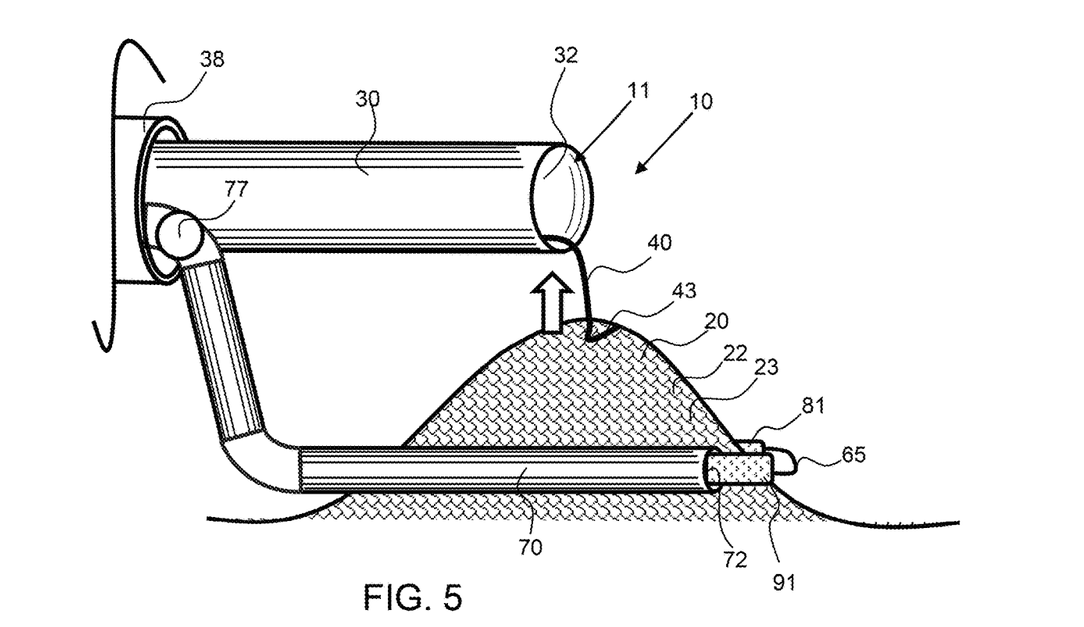
FIG. 5 shows a side perspective view of an exemplary magnetic endoscopic tissue inversion and resection device now advancing a first side first magnet and second side first magnet out of the distal ends of the first clamping tube and second clamping tube to pinch the plicated tissue therebetween.
Figure 6:
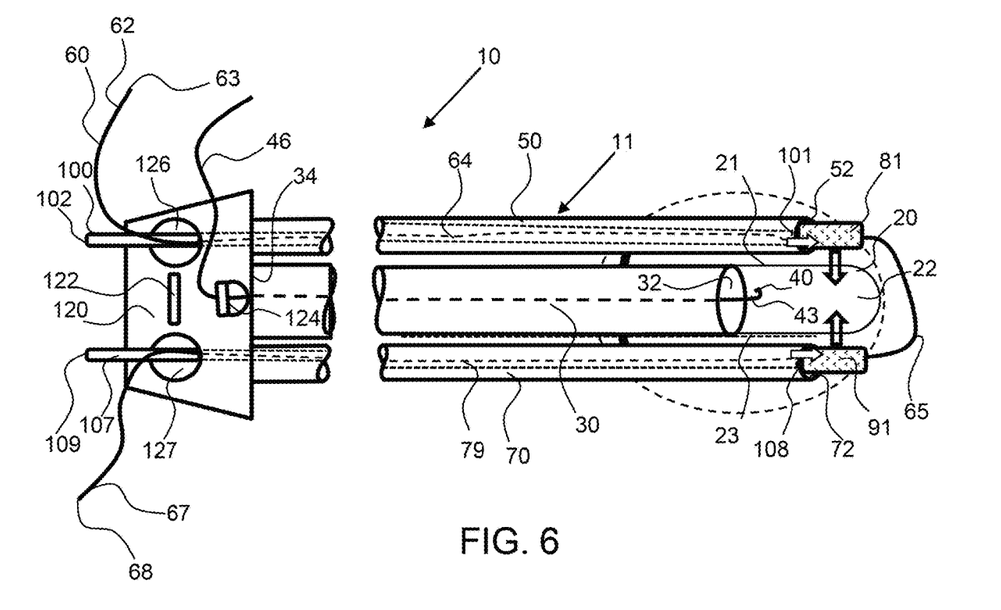
FIG. 6 shows a top perspective view of an exemplary magnetic endoscopic tissue inversion and resection device advancing a first side first magnet and second side first magnet out of the distal ends of the first clamping tube and second clamping tube to pinch the plicated tissue therebetween.

As shown in FIGS. 5 and 6, a first side first magnet 81 and second side first magnet 91 are being advanced out of the distal end openings 52, 72 of the first clamping tube 50 and second clamping tubes 70, respectively. The first side first magnet 81 is located on a first side 21 of the plicated tissue 22 and the second side first magnet 91 is configured on the second side 23 of the plicated tissue 22. Again, the magnets are coupled with the guide extension 60 and may be further positioned by manipulation of the guide extension.

Figure 7:
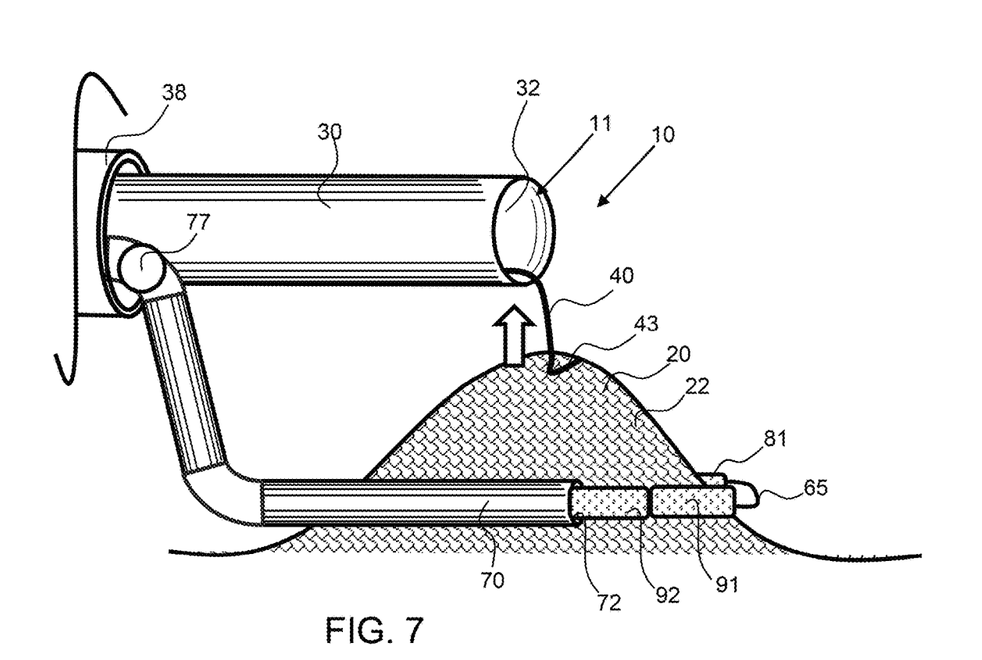
FIG. 7 shows a side perspective view of an exemplary magnetic endoscopic tissue inversion and resection device now advancing a first side second magnet and second side second magnet out of the distal ends of the first clamping tube and second clamping tube to pinch the plicated tissue therebetween.
Figure 8:
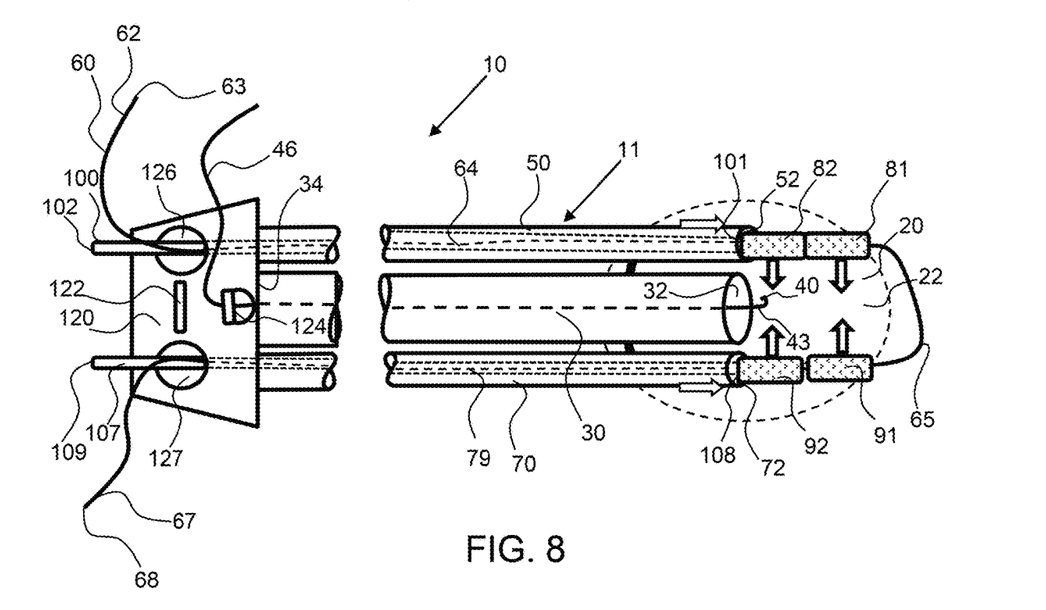
FIG. 8 shows a top perspective view of an exemplary magnetic endoscopic tissue inversion and resection device advancing a first side second magnet and second side second magnet out of the distal ends of the first clamping tube and second clamping tube to pinch the plicated tissue therebetween.

As shown in FIGS. 7 and 8, a first side second magnet 82 and second side second magnet 92 are being advanced out of the distal ends of the first clamping tube 50 and second clamping tube 70, respectively to pinch the plicated tissue therebetween. The magnets may be coupled to the guide extension 60 and inserted into the first clamping tube 50 and second clamping tube 70 through the first side clamping tube opening 126 and second side clamping tube opening 127 in the interface controller 120. As described herein, a plurality of magnets may be configured within each of the first clamping tube 50 and second clamping tube 70 upon insertion of the exemplary magnetic endoscopic tissue inversion and resection device 11 into the body.

Figure 9:
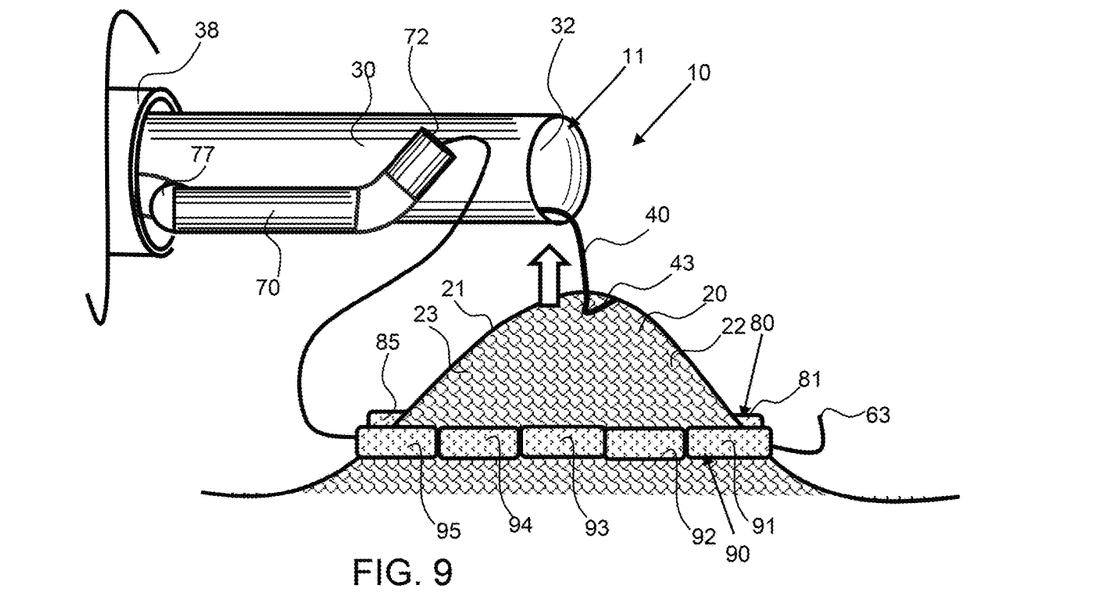
FIG. 9 shows a side perspective view of an exemplary magnetic endoscopic tissue inversion and resection device after a plurality of first side magnets and plurality of second side second magnets have been advanced to opposing sides of the plicated tissue and the guide extension being pulled from the magnets.
Figure 10:
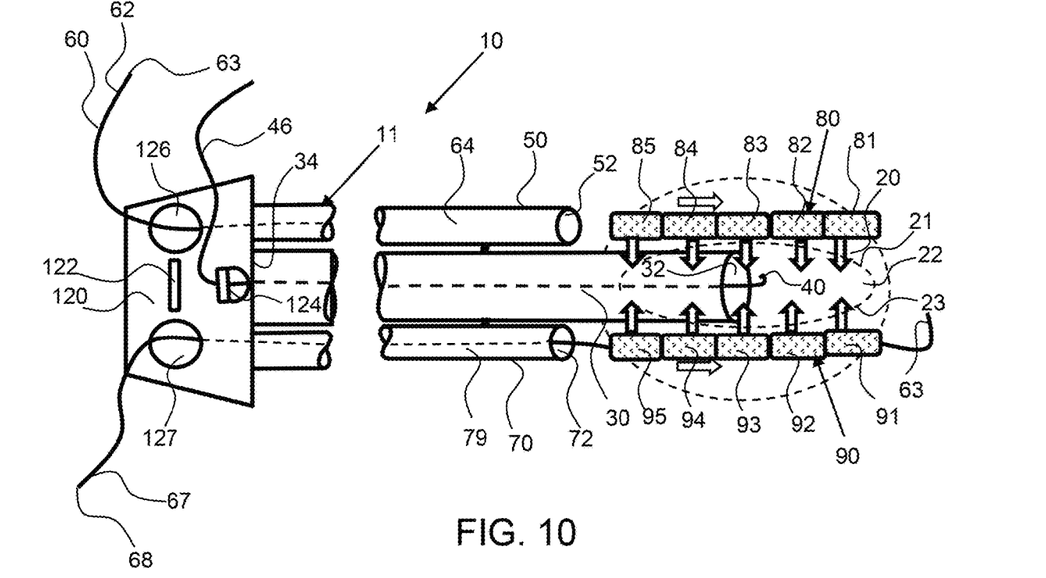
FIG. 10 shows a top perspective view of an exemplary magnetic endoscopic tissue inversion and resection device advancing a first side second magnet and second side second magnet out of the distal ends of the first clamping tube and second clamping tube to pinch the plicated tissue therebetween.

As shown in FIGS. 9 and 10, an exemplary magnetic endoscopic tissue inversion and resection device 11 has a plurality of first side magnets 80, including individual first side magnets 81, 82, 83, 84, 85 and plurality of second side magnets 90, including individual second side magnets 91, 92, 93, 94 and 95, on opposing sides of the plicated tissue and the guide extension 60 being pulled from the magnets. The first side magnets are configured on a first side 21 of the plicated tissue 22 and the second side magnets are configured on the second side 23 of the plicated tissue. The magnetic force, indicated by the large bold arrow pinches the plicated tissue together with an effective force to cause necrosis of the tissue therebetween and the tissue to join together in a joined region of tissue.

Figures 11, 12, 13:
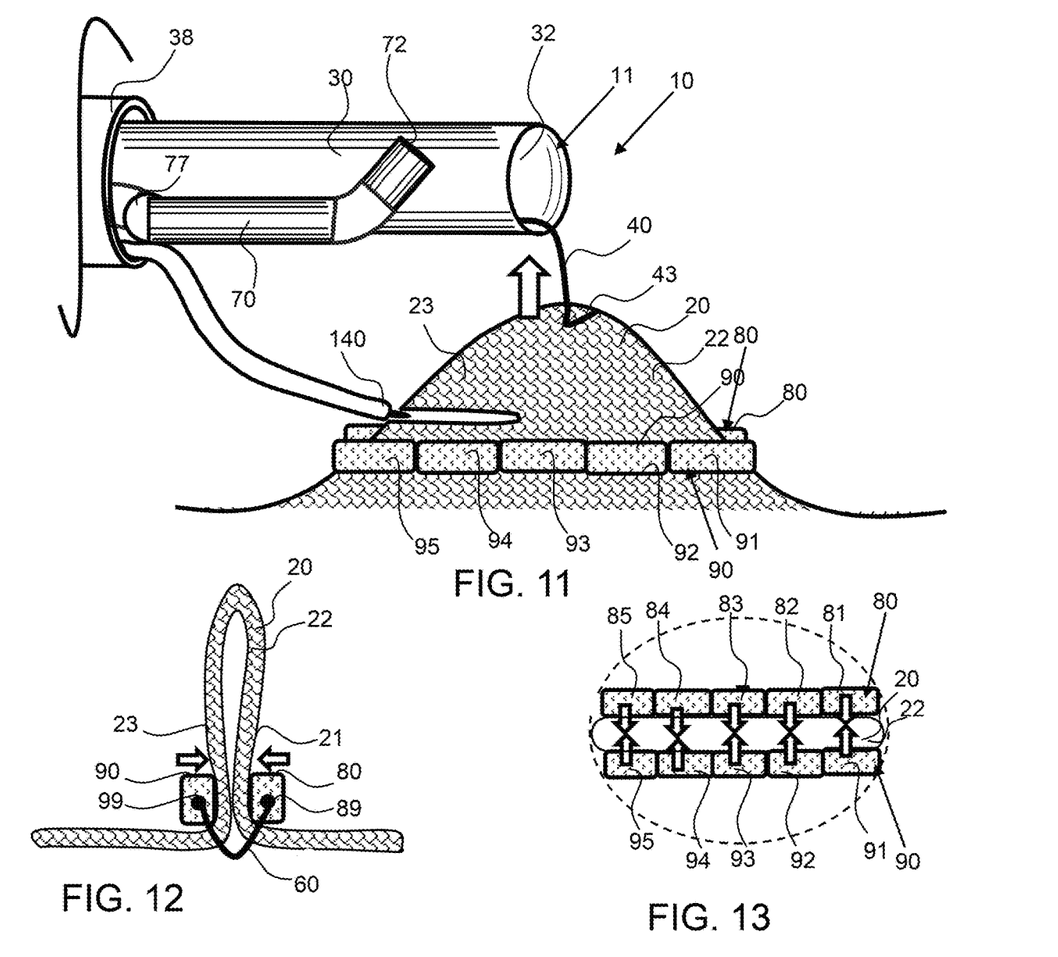
FIG. 11 shows a side perspective view of an exemplary magnetic endoscopic tissue inversion and resection device with a resecting tool cutting the plicated tissue between the plurality of magnets and the endoscope.
FIG. 12 shows an end view of the plicated tissue with the magnets clamping the plicated tissue.
FIG. 13 shows a top view of plicated tissue clamped together by a plurality of first side magnets and a plurality of second side magnets.

As shown in FIG. 11, an exemplary magnetic endoscopic tissue inversion and resection device 11 has a resecting tool 140 cutting the plicated tissue 22 between the plurality of first side magnets 80 and plurality of second side magnets 90 and the endoscope 30.

As shown in FIGS. 12 and 13, the plicated tissue 22 is configured with the magnets clamping the plicated tissue on opposing sides. The plurality of first side magnets 80 extend in a row along the first side 21 of the plicated tissue 20 and the plurality of second side magnets 90 extend in a row along the second side 23 of the plicated tissue. As shown in FIG. 12, the magnets 80, 90 have an aperture 89, 99 respectively for the guide extension 60 to extend therethrough to guide the magnets into position.

Figure 14:
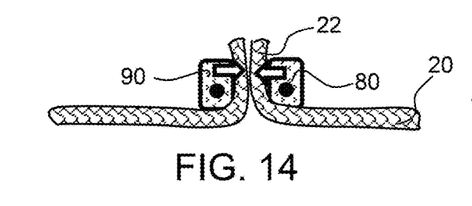
FIG. 14 shows an end view of plicated tissue clamped together by a first side magnet and a second side magnet and the tissue resected.

As shown in FIG. 14, the plicated tissue 22 is clamped together by first side magnets 80 and second side magnets 90 and the tissue is resected.

Figure 15:
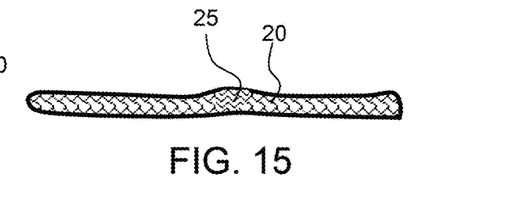
FIG. 15 shows the plicated tissue after it has healed together forming a joined region of tissue.

As shown in FIG. 15, the resected tissue is now healed together forming a joined region 25, a healed region of the resected tissue 20.

Figure 16:
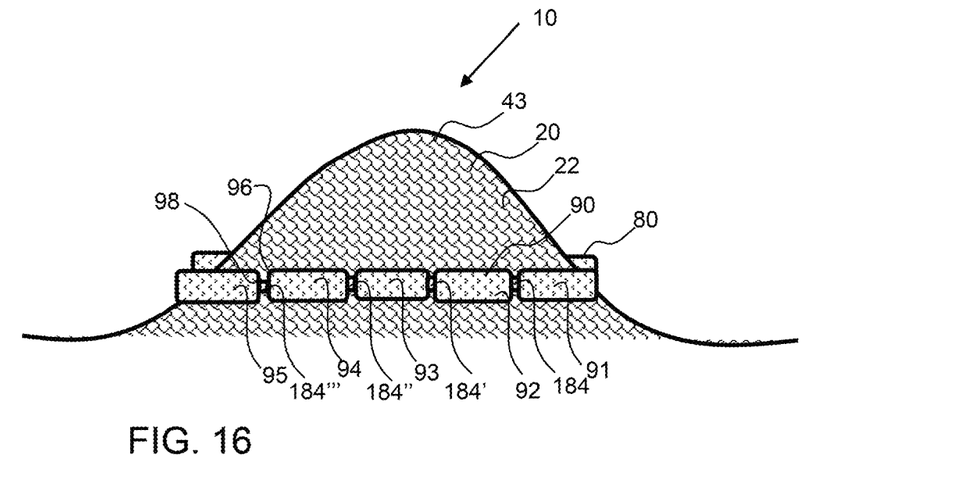
FIG. 16 shows plicated tissue clamped together by second side magnets having interconnecting features to couple the second side magnets together.

As shown in FIG. 16, the second side magnets 90 are coupled together by interconnecting features 184. The first second side magnet 91 is coupled to the second, second side magnet 92 by an interconnect feature 184. The second, second side magnet 92 is coupled to the third second side magnet 93 by an interconnect feature 184'. The third second side magnet 93 is coupled to the fourth second side magnet 94 by an interconnect feature 184". The fourth second side magnet 94 is coupled to the fifth second side magnet 95 by an interconnect feature 184'". As described herein, the interconnect feature may be configured to couple a proximal end 96 of a first magnet to a distal end 98 of a second magnet and may extend from the ends of the magnets. The interconnect feature may be a hook or interference fit feature or may be magnets of opposite poles that attract the adjacent magnet when brought into proximity with first magnet.

Figure 17:
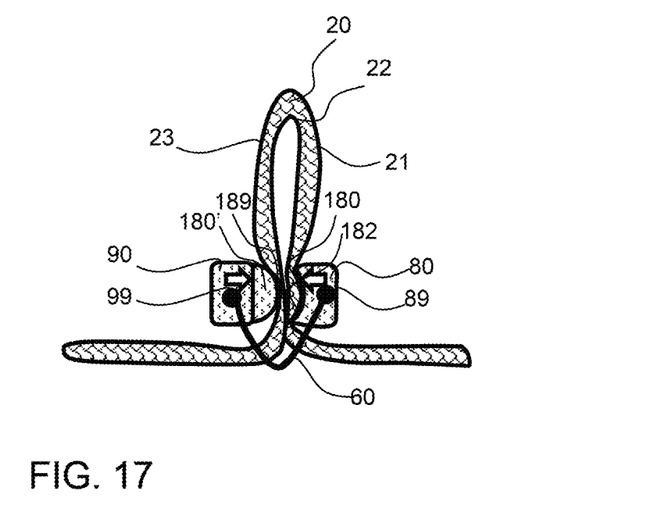
FIG. 17 shows an end view of plicated tissue clamped together by a first side magnet having a concave clamping surface and second side magnet having a convex clamping surface that nests into the concave clamping surface of the first side magnet to retain the plicated tissue therebetween.
Figure 18:
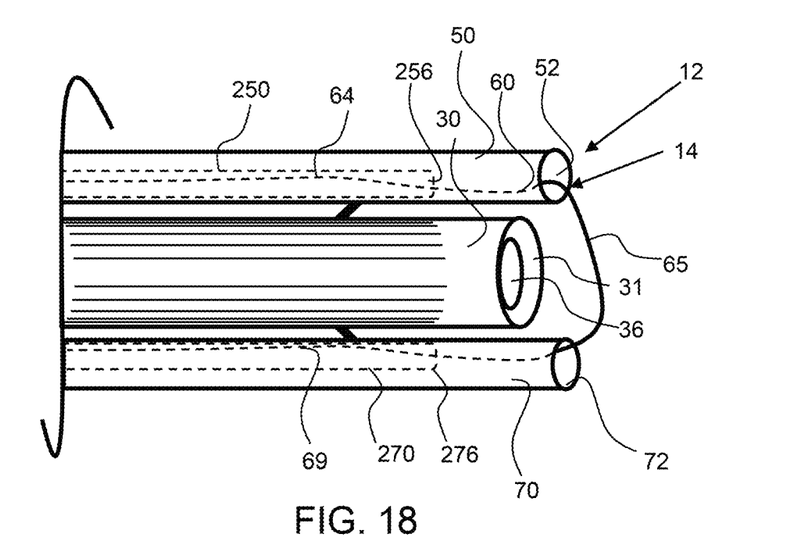
FIG. 18 shows a top perspective view of an exemplary endoscopic tissue inversion and resection system having an endoscope configured between a first clamping tube and second clamping tube and a first clamp component extending in the first clamping tube and a second clamp component extending in the second clamping tube.

As shown in FIG. 17, plicated tissue 22 is clamped together by a first side magnet 80 having a concave clamping surface 182 and second side magnet 90 having a convex clamping surface 189 that nests into the concave clamping surface of the first side magnet to retain the plicated tissue therebetween. The concave and convex surfaces are exemplary clamping surfaces 180, 180' respectively. The plicated tissue 22 is more effectively retained along this nesting arrangement of the clamping surfaces. The first side 21 and second side 23 of the plicated tissue 22 is shown in FIG. 17.

Referring now to FIGS. 18 to 21, an exemplary endoscopic tissue inversion and resection system 12 employs an endoscopic tissue inversion and resection device 14 including an endoscope 30 configured between a first clamping tube 50 and second clamping tube 70 and first clamp component 250 extending in the first clamping tube and a second clamp component 270 extending in the second clamping tube, both over the guide extension 60 that extends through each of clamping tubes and forms a loop portion 65 between the distal end opening 52 of the first clamping tube 50 and the distal end opening 72 of the second clamping tube 70. The guide extension 60 has a first tube extension 64, loop portion 65 and second tube extension 69.

Figure 19:
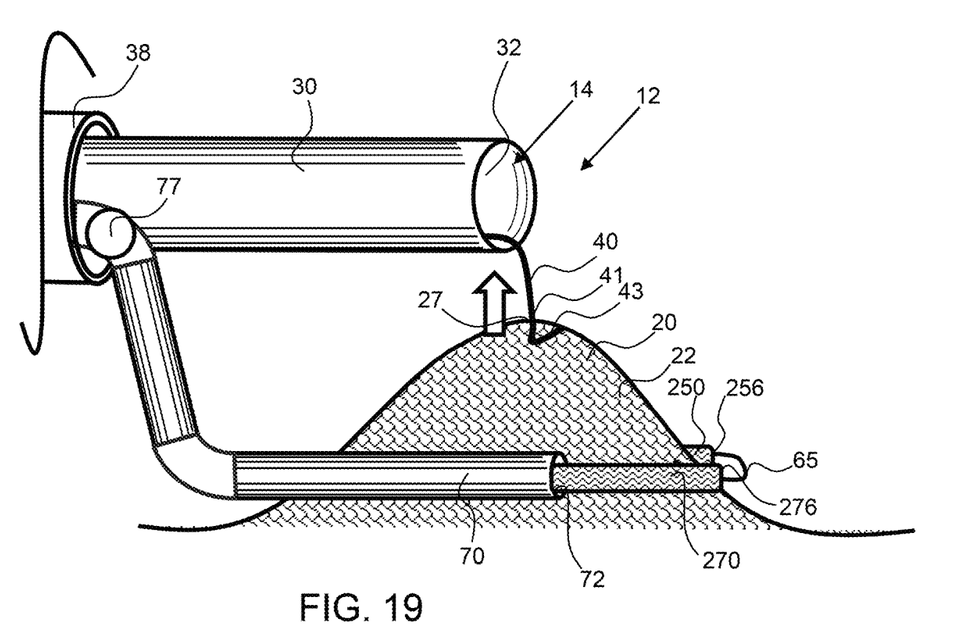
FIG. 19 shows a side perspective view of an exemplary endoscopic tissue inversion and resection device with the first clamp component extending out of the distal end opening of the first clamping tube and the second clamp component extending out of the distal end opening of the second clamping tube and both being advanced over the guide extension.

As shown in FIG. 19, a tissue grasping device 40 extends from the endoscope 30 and the tissue end 43 of the tissue grasping device grasps the tissue 20, such as by a hook 41, and pulls the tissue toward the endoscope 30, to from plicated tissue 22. With further reference to FIG. 19 and FIG. 19, the first clamp component 250 is advanced out and extends out of the distal end opening 52 of the first clamping tube 50 and the second clamp component 270 extends out of the distal end opening 72 of the second clamping tube 70 and both clamp components are being advanced over the loop portion 65 of the guide extension 60.

Figure 20:
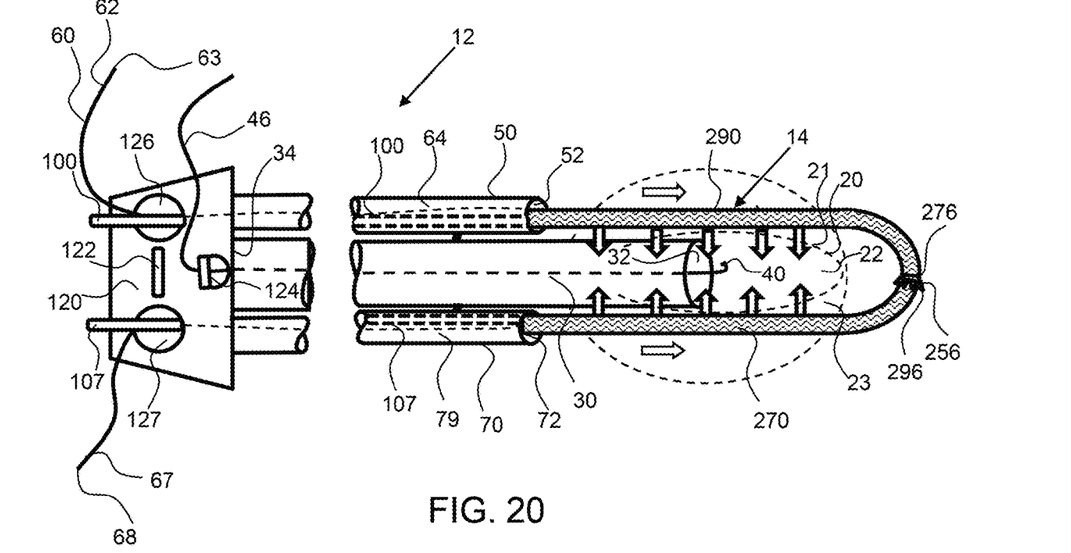
FIG. 20 shows a top perspective view of an exemplary endoscopic tissue inversion and resection device with the first clamp component extending out of the distal end opening of the first clamping tube and coupled to the second clamp component, extending out of the distal end opening of the second clamping tube, by a distal coupler.
Figure 21:
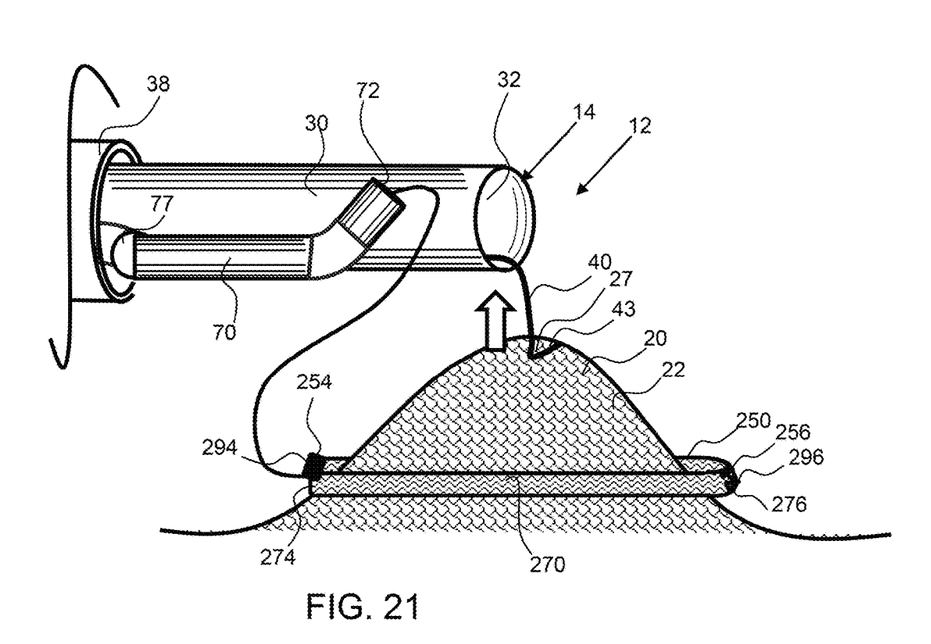
FIG. 21 shows a side perspective view of an exemplary endoscopic tissue inversion and resection device with the first clamp component extending on a first side of the plicated tissue coupled to the second clamp component extending along a second side of the plicated tissue by a distal coupler and a proximal coupler.

Referring now to FIGS. 20 and 21, the exemplary endoscopic tissue inversion and resection device 14 now has the first clamp component 50 advanced by the first side advancer 100 and extends out of the distal end opening 52 of the first clamping tube 50 and is coupled to the second clamp component 70, advanced by the second side advancer 107 and extends out of the distal end opening 72 of the second clamp component 70, by a distal coupler 296. The distal end 256 of the first clamp component 250 is coupled to the distal end 276 of the second clamp component 270 by advancement of the first and second clamp components into each other over the guide extension 60. As described herein, the distal coupler may be an integral distal coupler, wherein a portion of the first clamp component couples with a portion of the second clamp component. The first clamp component may have barbs that engage into apertures or openings in the second clamp component. Also, the first clamp component may be configured for insertion into the second clamp component, wherein barbs on the first clamp component latch into apertures of the second clamp component. As shown in FIG. 21, a proximal coupler 294 may couple together the proximal end 254 of the first clamp component 250 and the proximal end 274 of the second clamp component. With the distal and proximal ends of the clamp components coupled together, the plicated tissue 22 is restrained in a plicated state.

Figure 22:
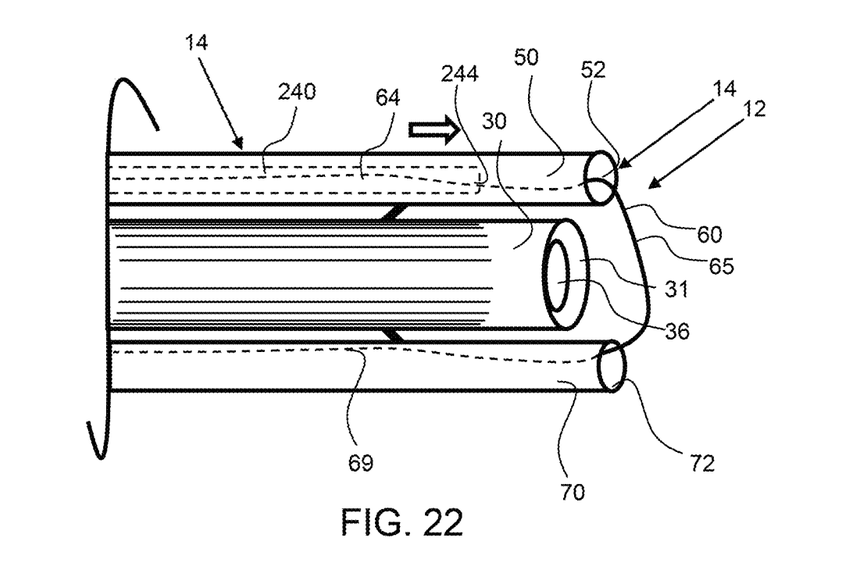
FIG. 22 shows a top perspective view of an exemplary endoscopic tissue inversion and resection system having an endoscope configured between a first clamping tube and second clamping tube and a clamp component extending in the first clamping tube and coupled with the guide extension.
Figure 23:
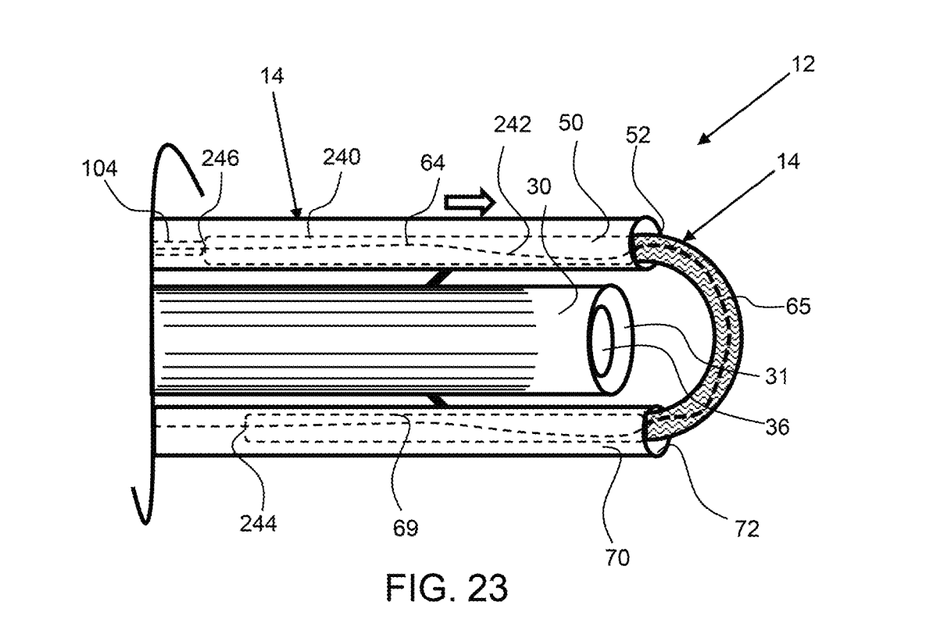
FIG. 23 shows a top perspective view of an exemplary endoscopic tissue inversion and resection system having an endoscope configured between a first clamping tube and second clamping tube and a clamp component extending in the first clamping tube, out of the distal end of the first clamping tube over the loop portion of the guide extension and through the distal end opening of the second clamping tube and into the second clamping tube.

Referring now to FIGS. 22 to 25, an exemplary endoscopic tissue inversion and resection system 12 employs endoscopic tissue inversion and resection device 14 having an endoscope 30 configured between a first clamping tube 50 and second clamping tube 70 and a clamp component 240 extending in the first clamping tube and coupled with the guide extension 60. The first end 244 of the clamp component 240 is shown in FIG. 22 and the first end 244 and second end 246 of the clamp component is shown in FIG. 23 as it is advanced through the clamping tubes. The clamp component may be a tube or form a conduit through which the guide extension extends. As shown in 22, the clamp component 240 is in the first clamping tube 50 and the guide extension 60 extends forming a loop portion 65 between the distal end opening 52 of the first clamping tube 50 and the distal end opening 72 of the second clamping tube 70.

As shown in FIG. 23, the exemplary endoscopic tissue inversion and resection system has the clamp component 240 now advanced by the advancer 104 to extend out of the first clamping tube 50, out of the distal end opening 52 of the first clamping tube along the loop portion 65 of the guide extension 60 and through the distal end opening 72 of the second clamping tube 70 and into the second clamping tube. The advancer may push the single clamp component and the guide extension 60 may guide the clamp component from the first clamping tube to the second clamping tube. The guide extension 60 has a first tube extension 64, loop portion 65 and second tube extension 69. The clamp component may be a shape memory material, such as nitinol, and may have a preform shape including the bend portion, that is the portion that forms the bend from a first side of the plicated tissue to the second side of the plicated tissue. This bend portion enables the clamp component to clamp the plicated tissue. As shown in FIG. 23, the bend portion 242 is not yet advanced out of the distal end opening 52 of the first clamping tube. The clamp component is forced to bend from the first clamping tube to the second clamping tube by the guide extension 60.

Figures 24, 25, 26:
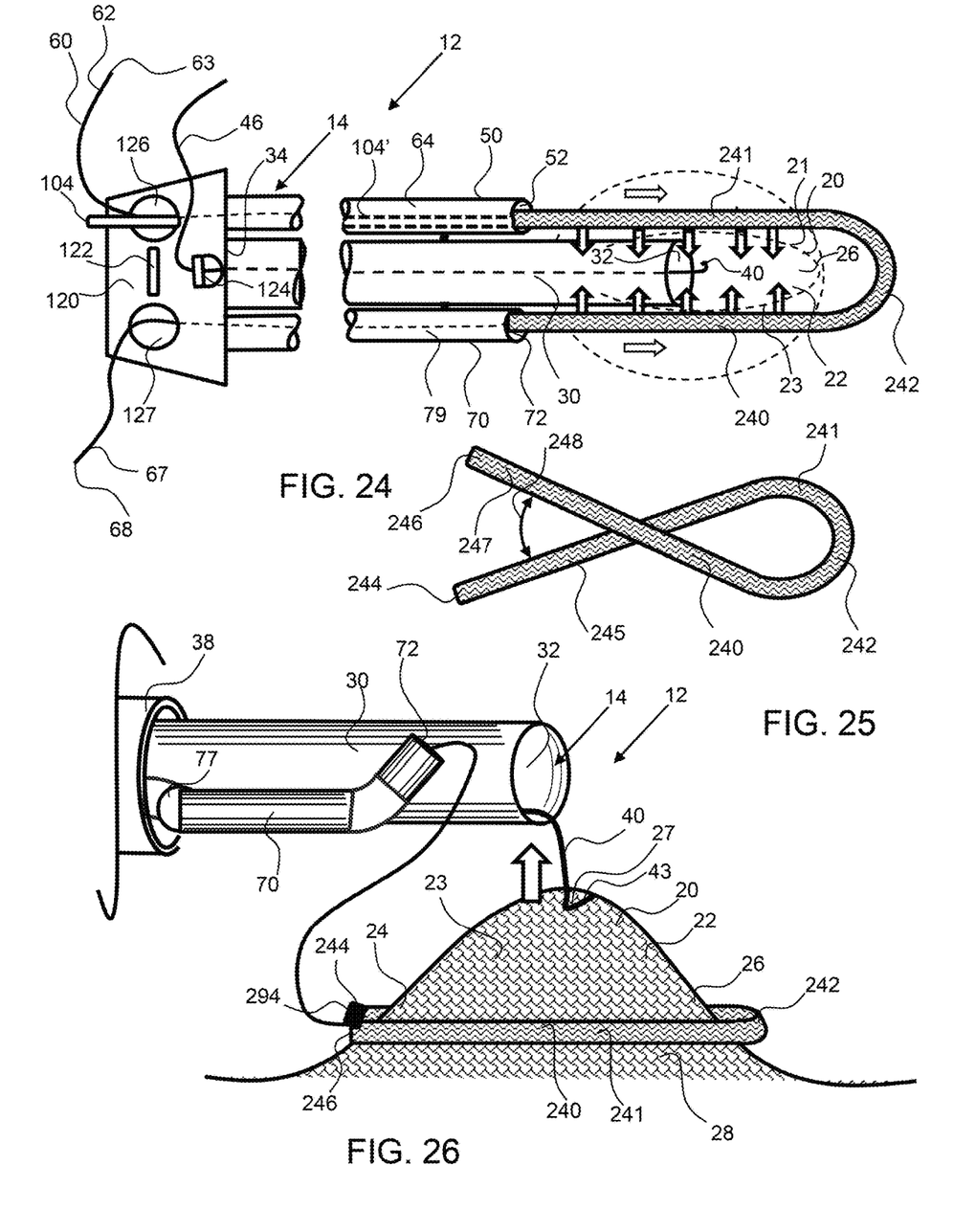
FIG. 24 shows a top view of an exemplary endoscopic tissue inversion and resection system with the first and second clamping tubes being pulled back with the bend portion of the clamp component configured around the distal end of the plicated tissue.
FIG. 25 shows a clamp component that has a bend portion that bends the clamp component more than 180 degrees such that the first end and second ends are overlapped in a preform shape.
FIG. 26 shows a side view of an exemplary endoscopic tissue inversion and resection system with the first and second clamping tubes actuated back to the endoscope and the clamp component clamping the plicated tissue to retain the plicated tissue along the base of the plication of said tissue.

Referring now to FIGS. 24 to 26 bend portion 242 of the clamp component 240, shape-memory clamp component 241, is now located at the distal end 26 of the plicated tissue 22 and forms the bend from the first side 21 to the second side 23 of the plicated tissue and produces a clamping force on the plicated tissue, at the base 28 of the plicated tissue, proximal to the beginning of the folded tissue. The advancer 104, 104' is pushing the shape-memory clamp component 241 out of the distal end opening 52 of the first clamping tube 50 and into the distal end opening 72 of the second clamping tube 70. As shown in FIG. 26, the clamping tubes are now actuated back toward the endoscope 30 and the clamp component 240 is clamping the plicated tissue 22 to retain the plicated tissue along the base 28 of said plicated tissue. A proximal coupler 294 may be configured on the first end 244 and second end 246 of the clamp component.

As shown in FIG. 25, a clamp component 240 has a bend portion 242 that bends the clamp component more than 180 degrees such that the first end 244 and second end 246 are overlapped in a preform shape. The first extension 245 and second extension 247 overlap in a preform shape from the bend portion 242 and form an overlap angle 248. The overlap angle 246 is the amount of bend greater than 180 degrees of the bend portion. As shown, the overlap angle 246 is about 45 degrees, making the bend portion bend the clamp component about 225 degrees. The bend portion may bend clamp component in a preform shape about 180 degrees or more, about 200 degrees or more, about 225 degrees or more, about 270 degrees or more about 300 degrees or more and any range between and including the bend angles provided. Note that a higher bend angle may create more force on the plicated tissue by the clamp extensions of a shape-memory clamp component.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A magnetic endoscopic tissue inversion and resection system comprising:
   a) an endoscope extending from a proximal end to a distal end;
   b) a first clamping tube and a second clamping tube coupled with the endoscope, each comprising a distal end opening;
   c) a guide extension that extends through the first clamping tube to the second clamping tube;
   d) a tissue grasping device coupled with the endoscope and having a grasper end configured to invert tissue between the first clamping tube and the second clamping tube to produce plicated tissue between the first clamping tube and second clamping tube;
   e) a plurality of magnets configured in each of the first clamping tube and the second clamping tube configured to move within the respective said first clamping tube and said second clamping tube and out of respective said distal end opening of said first clamping tube and said second clamping tube; and f) a first magnet advancer and a second magnet advancer, each configured to advance magnets of said plurality of magnets through respective said first clamping tube and said second clamping tube to configure the magnets on opposing sides of said plicated tissue
wherein a first side first magnet of said plurality of magnets is configured to move through the first clamping tube and contact a first side of plicated tissue, and wherein a second side first magnet of said plurality of magnets is configured to slide through the second clamping tube and contact a second side of plicated tissue; and
wherein the first side first magnet and the second side first magnet are configured to clamp the plicated tissue between them; and
wherein a first side first magnet has an interconnecting feature configured to couple with an interconnecting feature on a first side second magnet.

2. The magnetic endoscopic tissue inversion and resection system of claim 1, wherein the plurality of magnets are coupled with said guide extension.

3. The magnetic endoscopic tissue inversion and resection system of claim 2, wherein the plurality of magnets comprise an aperture and wherein the guide extension extends through said aperture.

4. The magnetic endoscopic tissue inversion and resection system of claim 1, wherein the plurality of magnets are permanent magnets.

5. The magnetic endoscopic tissue inversion and resection system of claim 1, wherein the plurality of magnets comprise a polymeric coating.

6. The magnetic endoscopic tissue inversion and resection system of claim 5, wherein the polymeric coating covers the plurality of magnet to prevent contact of the plurality of magnet with the tissue.

7. The magnetic endoscopic tissue inversion and resection system of claim 1, further comprising a third pair of magnets of said plurality of magnets.

8. The magnetic endoscopic tissue inversion and resection system of claim 1, wherein the tissue grasping device comprises a hook.

9. The magnetic endoscopic tissue inversion and resection system of claim 1, further comprising an imaging device coupled with the endoscope.

10. The magnetic endoscopic tissue inversion and resection system of claim 1, wherein the first clamping tube and the second clamping tube are made of a shape memory material.

11. The magnetic endoscopic tissue inversion and resection system of claim 1, further comprising a sheath that restrains the first clamping tube and second clamping tube, wherein the first clamping tube and second clamping tube are configured to automatically actuate to a preset shape away from the endoscope and with said offset distance upon sliding the sheath back toward the proximal end of the endoscope.

12. The magnetic endoscopic tissue inversion and resection system of claim 1, wherein the guide extension is a suture.

13. The magnetic endoscopic tissue inversion and resection system of claim 1, wherein the guide extension is a guide wire.

14. The magnetic endoscopic tissue inversion and resection system of claim 1, wherein the interlocking feature of the first side first magnet is a magnet configured on an end of said first side first magnet and wherein the interlocking feature of the first side second magnet is a magnet configured on an adjacent end of the first side second magnet to said end of the first side first magnet.

15. The magnetic endoscopic tissue inversion and resection system of claim 1, wherein the interlocking feature is configured to couple the first side first magnet to the first side second magnet in the first clamping tube.

16. The magnetic endoscopic tissue inversion and resection system of claim 1, wherein the interlocking feature is configured to couple the first side first magnet to the first side second magnet when the first side second magnet is advanced out of the first clamping tube.

17. A magnetic endoscopic tissue inversion and resection system comprising:
a) an endoscope extending from a proximal end to a distal end;
b) a first clamping tube and a second clamping tube coupled with the endoscope, each comprising a distal end opening;
c) a guide extension that extends through the first clamping tube to the second clamping tube;
d) a tissue grasping device coupled with the endoscope and having a grasper end configured to invert tissue between the first clamping tube and the second clamping tube to produce plicated tissue between the first clamping tube and second clamping tube;
e) a plurality of magnets configured in each of the first clamping tube and the second clamping tube configured to move within the respective said first clamping tube and said second clamping tube and out of respective said distal end opening of said first clamping tube and said second clamping tube; and
f) a first magnet advancer and a second magnet advancer, each configured to advance magnets of said plurality of magnets through respective said first clamping tube and said second clamping tube to configure the magnets on opposing sides of said plicated tissue;
wherein a first side first magnet of said plurality of magnets is configured to move through the first clamping tube and contact a first side of plicated tissue, and wherein a second side first magnet of said plurality of magnets is configured to slide through the second clamping tube and contact a second side of plicated tissue; and
wherein the first side first magnet and the second side first magnet are configured to clamp the plicated tissue between them; and
wherein the first side first magnet has a clamping surface and wherein the second side first magnet has a clamping surface configured to nest into the clamping surface of the first side first magnet to clamp and restrain the plicated tissue along the convex surface and concave surface.

18. The magnetic endoscopic tissue inversion and resection system of claim 17, wherein the first side first magnet has concave clamping surface and wherein the second side first magnet has a convex clamping surface configured to nest into the concave clamping surface of the first side first magnet to clamp and restrain the plicated tissue along the convex surface and concave surface.

* * * * *